US012746011B2

(12) United States Patent
McAfee et al.

(10) Patent No.: US 12,746,011 B2
(45) Date of Patent: Sep. 29, 2026

(54) DIRECT PRESSURE DEVICE

(71) Applicant: Altitude Technologies, Inc., Tulsa, OK (US)

(72) Inventors: Marissa McAfee, Cumming, GA (US); Rowdy Reeves, Tulsa, OK (US); Cliff Laymon, Tulsa, OK (US)

(73) Assignee: Altitude Technologies, Inc., Tulsa, OK (US)

( * ) Notice: Subject to any disclaimer, the term of this patent is extended or adjusted under 35 U.S.C. 154(b) by 50 days.

(21) Appl. No.: 18/932,103

(22) Filed: Oct. 30, 2024

(65) Prior Publication Data

US 2025/0134532 A1 May 1, 2025

Related U.S. Application Data

(60) Provisional application No. 63/546,433, filed on Oct. 30, 2023.

(51) Int. Cl.
*A61B 17/132* (2006.01)

(52) U.S. Cl.
CPC ................................ *A61B 17/1325* (2013.01)

(58) Field of Classification Search
CPC . A61B 17/1327; A61B 17/132; A61B 17/128; A61B 17/122; A61B 17/12; A61B 17/0057; A61B 17/1325; A61B 17/135; A61B 2017/00659; A61B 2017/00676; A61B 2017/00778; A61B 2017/12004; A61F 5/32; A61F 5/30; A61F 2013/0028; A61F 2013/00106; A61F 2013/00468;
(Continued)

(56) References Cited

U.S. PATENT DOCUMENTS 10,463,378 B2 11/2019 Dou
11,020,127 B2 6/2021 Popp
12,396,736 B2 * 8/2025 Clark .................. A61B 17/085
(Continued)

FOREIGN PATENT DOCUMENTS

CN 210433519 U 5/2020
CN 217244624 U 8/2022
(Continued)

OTHER PUBLICATIONS

International Search Report and Written Opinion received in co-pending PCT International Patent Application No. PCT/US24/53740; Korean Intellectual Property Office, Feb. 10, 2025.
(Continued)

*Primary Examiner* — Andrew Restaino
(74) *Attorney, Agent, or Firm* — Head, Johnson, Kachigian & Wilkinson PC

(57) ABSTRACT

A direct pressure device, which may be a device designed to hold direct pressure to a wound that has been packed with a hemostatic agent or to control distal hemorrhage by maintaining pressure to a pressure point. The direct pressure device may be designed to be used with two tourniquets or an elastic wrap/ACE wrap-type device to apply downward pressure to control bleeding from a wound or to apply pressure to a pressure point. The direct pressure device may be a small, lightweight, versatile device that is inexpensive and portable, which may enable it to reach those within the field that need it.

8 Claims, 12 Drawing Sheets

(58) Field of Classification Search
CPC ........ A61H 1/008; A61H 7/001; A61H 39/04; A61M 2025/028
See application file for complete search history.

(56) References Cited

U.S. PATENT DOCUMENTS

| | | | | |
|---|---|---|---|---|
| 2006/0118679 | A1 * | 6/2006 | Delgado | G06F 3/039 248/118 |
| 2013/0267994 | A1 * | 10/2013 | Crowder | A61B 17/1325 606/203 |
| 2014/0163442 | A1 * | 6/2014 | Lee | A61H 7/005 601/134 |
| 2020/0121327 | A1 * | 4/2020 | Burkart | A61B 17/1327 |

FOREIGN PATENT DOCUMENTS

| | | | | |
|---|---|---|---|---|
| CN | 115670572 A | | 2/2023 | |
| DE | 3133793 | * | 3/1983 | A61B 17/12 |
| KR | 10-2428445 B1 | | 8/2022 | |

OTHER PUBLICATIONS https://safeguardmedical.com/products/tq-ram.
JETT Emergency Treatmwnt Tool; https://www.narescue.com/junctionaI-emergency-treatment-tool-jett.html?srsltid=AfmBOopcSMzG7ba7xfZW4FTJnT930alowRP3bToMQRJns4aFVOmbsnp4.
https://safeguardmedical.com/products/croc%C2%AE-combat-ready-Clamp.
McAfee, "Casualty Care Improvised Direct Pressure Adjunct" Society for Science, 2018.
https://rescue-essentials.com/aajts-abdominal-aortic-junctional-tourniquet/.
Theodoridis et al. "Evaluation and Testing of Junctional Tourniquets by Special Operation Forces Personnel: A Comparison of the Combat Ready Clamp and the Junctional Emergency Treatment Tool"; Jpurnal of Special Operations Medicine, 2016 Spring;16(1):44-50.
Woodson, M.D., "Combat Ready Clamp™ Addition to the Tactical Combat Casualty Care Guidelines Jul. 2011" Defense Health Board, Sep. 2011.
https://www.sammedical.com/products/sam-junctional-tourniquet.

* cited by examiner

DIRECT PRESSURE DEVICE

CROSS REFERENCE

This application is based on and claims priority to U.S. Provisional Application No. 63/546,433 filed Oct. 30, 2023.

BACKGROUND OF THE INVENTION

Field of the Invention

This invention relates generally to a direct pressure device and more particularly, but not by way of limitation, to a user-friendly device used in the prehospital setting to provide rapid arterial occlusion of an extremity by providing direct pressure over an artery or wound.

Description of the Related Art

When a person is injured, it is often necessary to provide pressure to the wound to minimize blood loss. Even a wound that has been packed with hemostatic gauze must have pressure held over the hemostatic gauze for three minutes once the wound has been packed. This is particularly challenging when the patient is suffering from multiple wounds that all require attention or when multiple people are injured. In such a circumstance, it may not be possible for emergency medical personnel to maintain pressure by hand to every wound. Current devices on the market are too bulky, heavy, and expensive to allow them to reach all medical and non-medical professionals on the front lines who have need for such devices.

Uncontrolled hemorrhage is the leading cause of preventable death in the battlefield and the mortality rate for junctional hemorrhage in the field is exceptionally high. Regular extremity tourniquets consist of straps that are wrapped around an arm or leg and tightened until the bleeding stops. These are very difficult to use for a junctional area hemorrhage, which is bleeding at the transition zones between extremities and the torso where major vascular structures pass through. Junctional wounds are larger and anatomically more complex than distal extremity wounds, posing a greater risk of ischemic injury to the limb and damage to neighboring structures and organs. The fact that junctional hemorrhage is still a leading cause of mortality in combat is partly due to the difficulty of using the current approved devices. The current devices are expensive, cumbersome, and during emergency situations when fine motor skills are diminished, they are of limited usefulness. These drawbacks are of additional concern to emergency medical services in low-income communities and countries that suffer from a high burden of trauma.

Based on the foregoing, it is desirable to provide a direct pressure device that may be used to provide consistent pressure to a wound.

It is further desirable for the direct pressure device to attach directly to a tourniquet, bandage, or improvised belt.

It is further desirable for the direct pressure device to be able to be used to apply direct pressure to an artery or placed over a wound packed with hemostatic gauze.

It is further desirable for the direct pressure device to be used in military and emergency medical markets, as well as clinical applications.

It is further desirable for the direct pressure device to be a small, lightweight, versatile device that is inexpensive and portable, which may enable it to reach those within the field that need it.

SUMMARY OF THE INVENTION

In general, in a first aspect, the invention relates to a direct pressure device comprising a deck and a body projecting perpendicularly from the deck and terminating in an apex. The body may be an apex pylon, and the direct pressure device may further comprise a plurality of apex supports extending at an angle both in the direction of the deck and outward from the apex. A plurality of cross members may extend radially outward from the apex pylon at a location spaced from the deck but closer to the deck than the apex, where the apex supports each connect to the one of the cross members, extending from the apex to the cross members. The cross members may each terminate in a tie down, each of which may curve outwardly front to back such that they project outwardly relative to both the apex supports and the deck. The direct pressure device may further comprise landing gear extending horizontally outward from the apex or from the apex supports. The landing gear may be L-shaped, connecting on one end to the apex or one of the apex supports and on an opposing end to one of the cross members.

Alternately, the body may be frustoconical. The direct pressure device may further comprise landing gear extending outward from the body.

The direct pressure device may further comprise a ledge projecting backward and inward from one side of an edge of a back of the deck, where the ledge projects inward to create a gap between a projecting portion of the ledge and the deck, and/or a blade connected to one side of an edge of a back of the deck, where the blade projects inward to lie in a plane parallel to, but spaced from, the deck to create a gap therebetween.

The direct pressure device may further comprise one or more tourniquets and/or elastic wraps.

Figure 2:
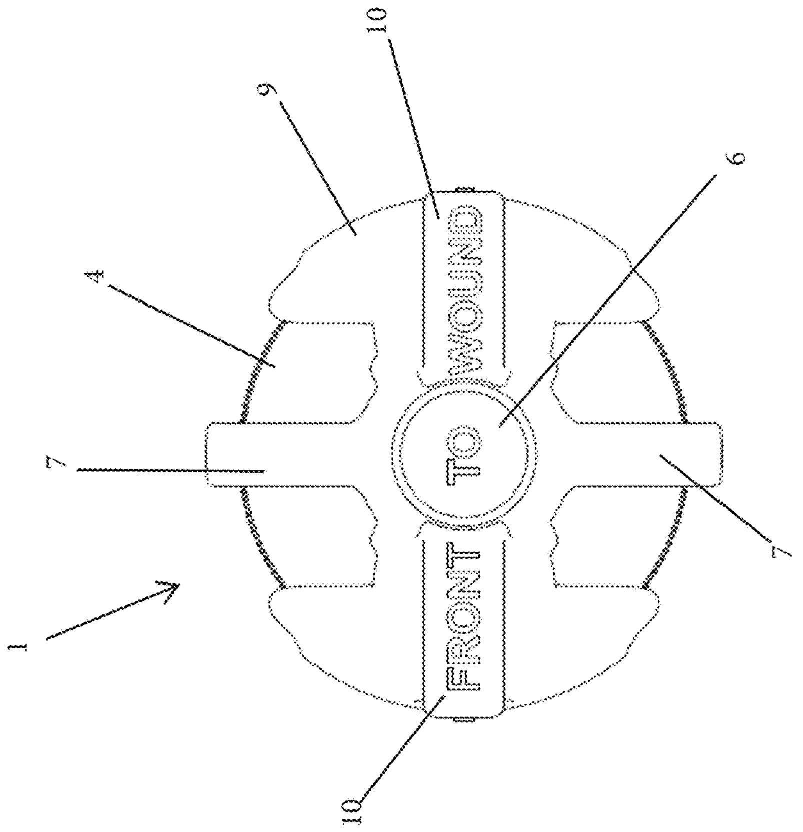
FIG. 2 is a front view thereof.
Figure 1:
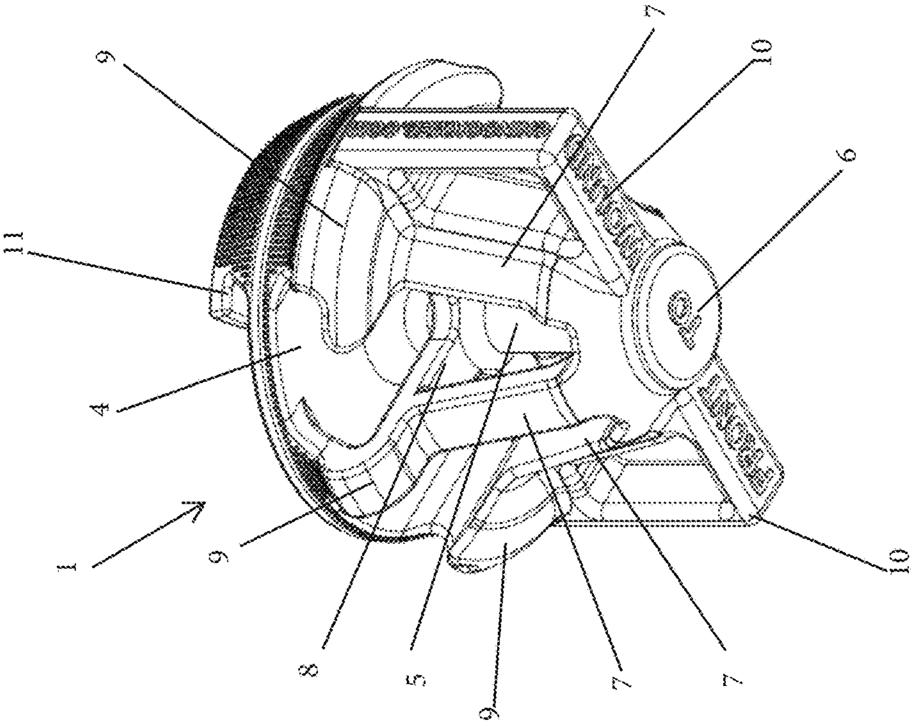
FIG. 1 is a front perspective view of the direct pressure device of the present invention.
Figure 4:
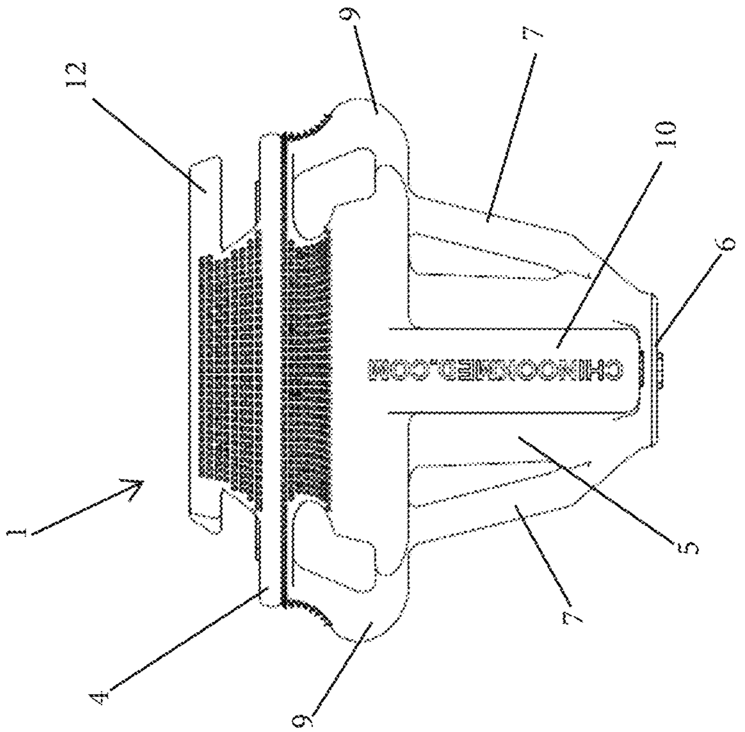
FIG. 4 is a side view thereof.
Figure 3:
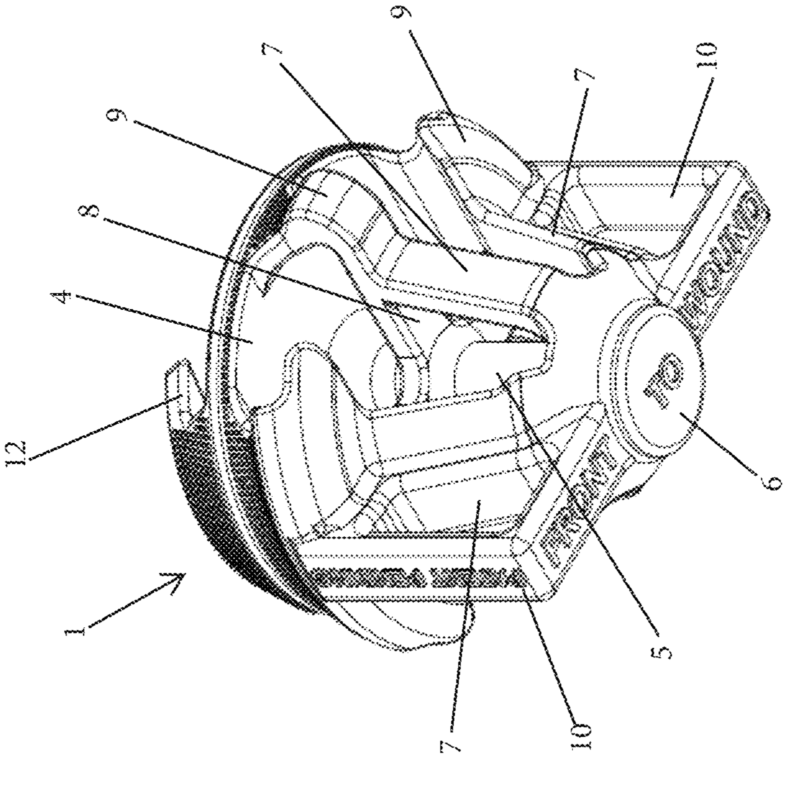
FIG. 3 is a side perspective view thereof.
Figure 6:
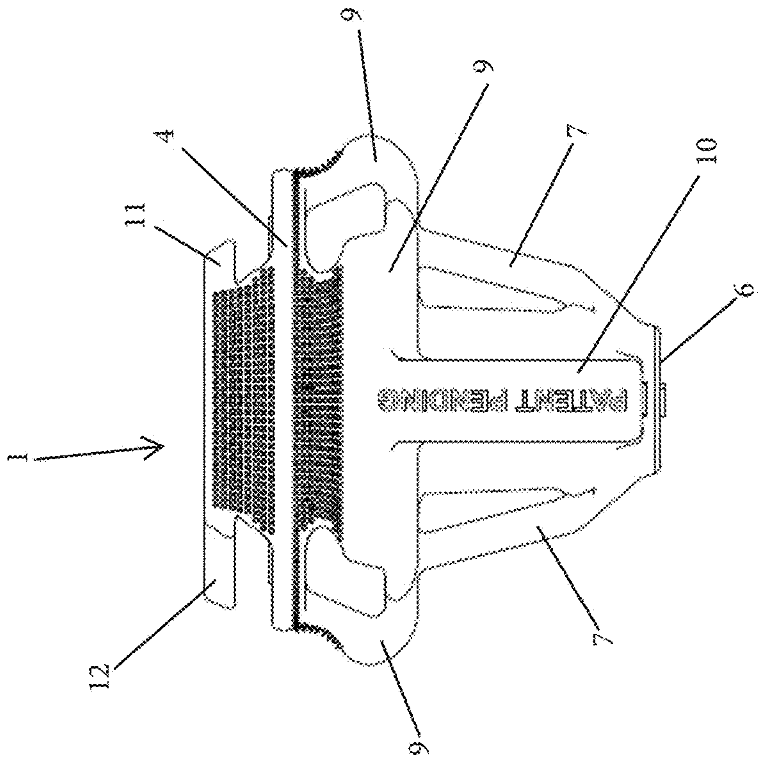
FIG. 6 is an alternate side view thereof.
Figure 5:
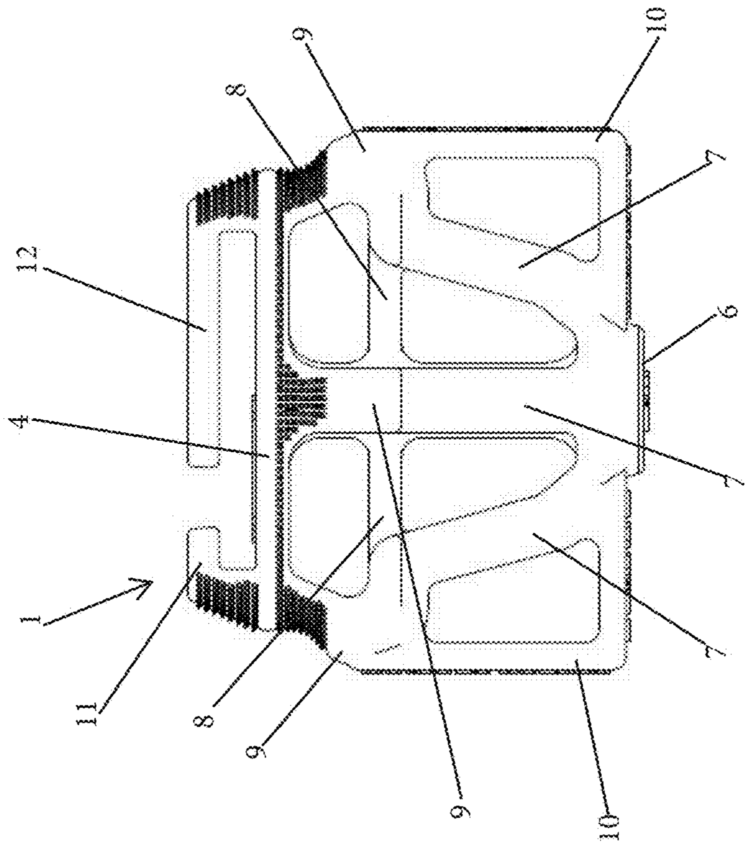
FIG. 5 is an alternate side view thereof.
Figure 7:
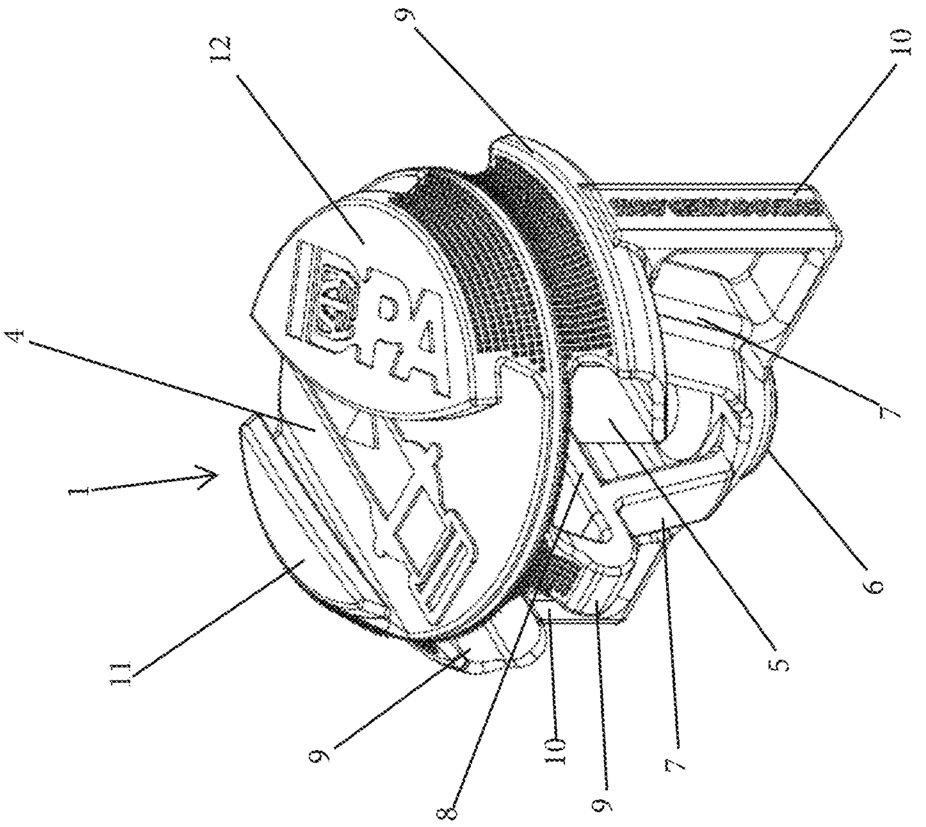
FIG. 7 is a back perspective view thereof.
Figure 8:
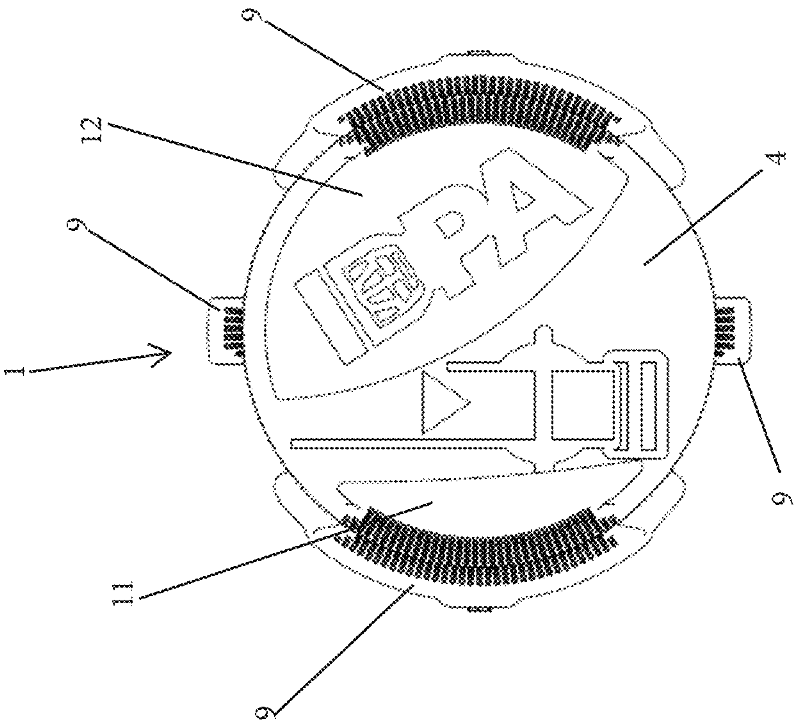
FIG. 8 is a back view thereof.
Figure 9:
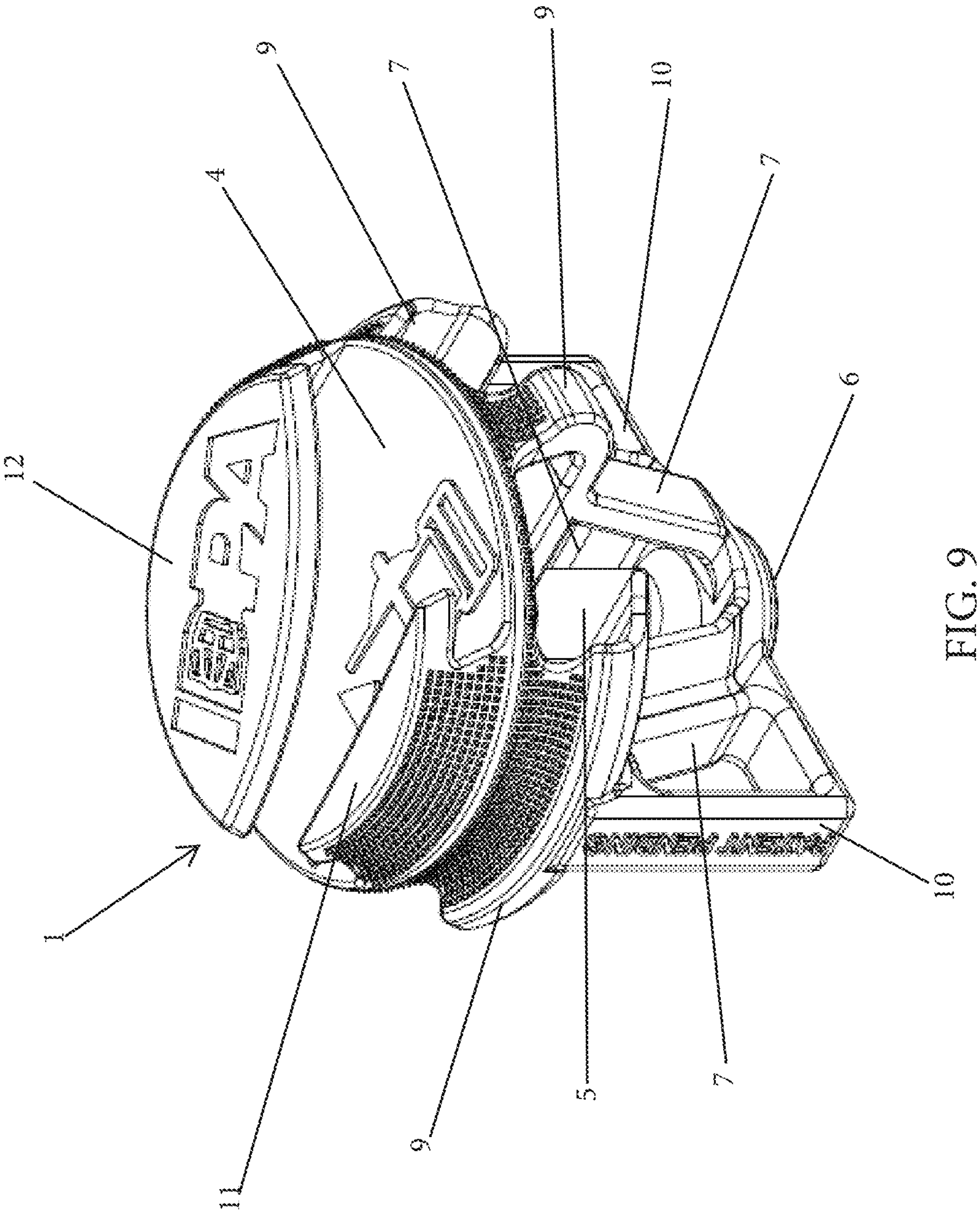
FIG. 9 is a back perspective view thereof.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

In general, in a first aspect, the invention relates to a direct pressure device 1. The direct pressure device 1 may be a device designed to hold direct pressure to a wound that has been packed with a hemostatic agent or to control distal hemorrhage by maintaining pressure to a pressure point. The direct pressure device 1 may be designed to be used with tourniquet(s) 2 or elastic wrap/ACE wrap-type device(s) 3 to apply downward pressure to control bleeding from a wound or to apply pressure to a pressure point. The direct pressure device 1 may be a small, lightweight, versatile device that is inexpensive and portable, which may enable it to reach those within the field that need it.

The direct pressure device 1 may have a deck 4 with an apex pylon 5 projecting horizontally from the deck 4 and terminating in an apex 6. The apex 6 may be circular or any other desired shape and may be generally flat, lying in a plane parallel to that of the deck 4, with the apex pylon 5 having an axis running perpendicular to both planes. A plurality of apex supports 7 may extend at an angle both in the direction of the deck 4 and outward from the apex 6 to support the apex 6. For example, four apex supports 7 may extend from the apex 6: one to the right, one to the left, one to the top, and one to the bottom, as shown, or any other number and arrangement of apex supports 7, as desired. The apex supports 7 may be evenly spaced, as shown, or unevenly spaced, as desired. A plurality of cross members 8 may extend radially outward from the apex pylon 5 at a location spaced from the deck 4, but closer to the deck 4 than the apex 6. For example, four cross members 8 may extend radially and perpendicularly outward from the apex pylon 5: one to the right, one to the left, one to the top, and one to the bottom, as shown, or any other number and arrangement of cross members 8. The number and arrangement of cross members 8 may correspond to the number and arrangement of apex supports 7 and the apex supports 7 may each connect to the one of the cross members 8, extending from the apex 6 to the cross members 8. Each of the cross members 8 may terminate in a tie down 9, which may curve outwardly front to back such that they project outwardly relative to both the apex supports 7 and the deck 4. Landing gear 10 may extend horizontally outward from the apex 6 or from the apex supports 7 just below the apex 6, as shown. The direct pressure device may include two sets of landing gear 10, as shown, with one extending to the right and one extending to the left. The landing gear 10 may be generally L-shaped, initially extending to the sides horizontally outward before bending at a 90-degree angle and continuing to extend backward horizontally in the direction of the deck 4. The landing gear 10 may connect to the tie downs 9 of the right and left cross members 8, as shown. The tie downs 9 may all slightly curve, defining segments of the same circle, and the tie downs 9 to the right and left, where the landing gear 10 connects, may have a greater arc length than that of the tie downs 9 at the top and bottom of the direct pressure device 1. The backs of the tie downs 9, which may connect to the deck 4, may be generally textured.

Alternately, as shown in FIGS. 14 through 21, the direct pressure device 1 may be solid between the deck 4 and the apex 6, having a generally frustoconical shape therebetween, with the landing gear 10 extending therefrom.

The deck 4 may have a ledge 11 projecting backward and inward from one side of the edge of the back of the deck 4 and a blade 12 connected to the opposing side of the edge of the back of the deck 4. The shape of the blade is significant in the way it interfaces with the tourniquet or ace wrap. The unique shape and orientation of the blade secures the tourniquet to the deck by fitting between the tourniquet base plate and windless strap material. While only connecting along the edge of the deck 4, the blade 12 may project inward to lie in a plane parallel to, but spaced from, the deck 4, creating a gap therebetween. The ledge 11 similarly may have a portion that projects inward, but to a lesser extent than the blade 12, also creating a gap between the deck 4 and the projecting portion of the ledge 11. The outside surfaces of the ledge 11, the blade 12, and the connections between the ledge 11 and blade 12 and the deck 4 may be generally textured.

During use, the apex 6 may be pointed toward the wound while a portion of the tourniquets 2 and/or wrap 3 fit into the gap between the deck 4 and the projecting portion of the ledge 11 and the blade 12 and press against the back of the deck 4. The deck 4 may secure tie downs, such as tourniquets, straps, or wraps, while the apex 6 provides direct pressure to stop the flow of blood. The landing gear 10 may provide stabilization to keep the device in place and keep it from rolling when pressure is applied.

Optionally, the direct pressure device 1 may have a secondary strap that can be used in conjunction with just one of the tourniquets 2. When this strap is used with a sled device, it may allow for the application of two adjuncts 1 on the same patient in the event of bilateral inguinal bleeding. This strap may also be used as an axillary strap, which would allow for the treatment of massive bleeding coming from the armpit/axilla by allowing the compression of the subclavian-brachial artery.

During use, the direct pressure device 1 may be used in conjunction with two tourniquets 2 or an elastic wrap/ACE wrap-type device 3 to apply downward pressure to control bleeding from a wound or to apply pressure to a pressure point. The direct pressure device may operate with the three most prevalent tourniquets (TQ) 2 on the market, namely CAT, SOFT, and SAM-XT and elastic wraps 3, or any other desired device. The following are example step-by-step instructions outlining how to prepare different TQs 2 or wrap 3, attach the direct pressure device 1, and apply the adjunct for each of the four applications. These are merely examples, as the direct pressure device 1 may be used with the TQs 2 or elastic wraps 3 in different ways or with different securing devices, as desired.

CAT Application

Figure 10:
FIG. 10 is a perspective view of the direct pressure device of the present invention in use.

The CAT application is shown in FIG. 10. Attaching the two TQs 2 together: insert the tip of the second TQ's band through the first TQ's buckle. Feed the TQ band through the buckle until the tip of the band touches the windless clip but does not pass. Secure the hook and loop material back onto itself to ensure the TQ is close to appropriate size and to help keep the hook and loop material from sticking to the patient or the provider's uniform. Once connected, you are ready to attach the direct pressure device 1.

Attaching the device: hold the direct pressure device 1 in your left hand with the wide portion of the clip face up and toward the thumb, with the leaf at the bottom left of the palm. Hold the CAT in the right hand with the buckle facing away from you. Ensure the leaf of the direct pressure device 1 slides under all layers of fabric under the windless and slide the TQ 2 all the way left under the clip. Slide the CAT all the way right.

Applying the adjunct: now that the direct pressure device 1 is in place, visually inspect to ensure the device is properly prepped. Place the direct pressure device 1 in your right hand with the adjunct facing up and slide it under the patient's lower back, using a sawing motion to work the TQ 2 strap midway down the glute. Ensure the direct pressure device 1 is slightly offset from the desired area/pressure point, to the strap side, not the buckle side, of the device. Place the TQ 2 band through the open buckle, then stabilize the direct pressure device 1 with your non-dominant hand while simultaneously pulling the TQ2 band with your dominant hand. Ensure the TQ 2 is as tight as it can get with no slack before securing the strap back onto itself via the hook and loop material. Once the TQ 2 band is as tight as it can get and the direct pressure device 1 is flat against the patient's skin directly over the desired area/pressure point, secure the hook and loop material all the way around. Twist the windless until the bleeding has stopped. This may take two to six twists, depending on how tight the TQ 2 band was before starting to twist the windless. Finally, secure the windless.

SAM-XT Application

Figure 11:
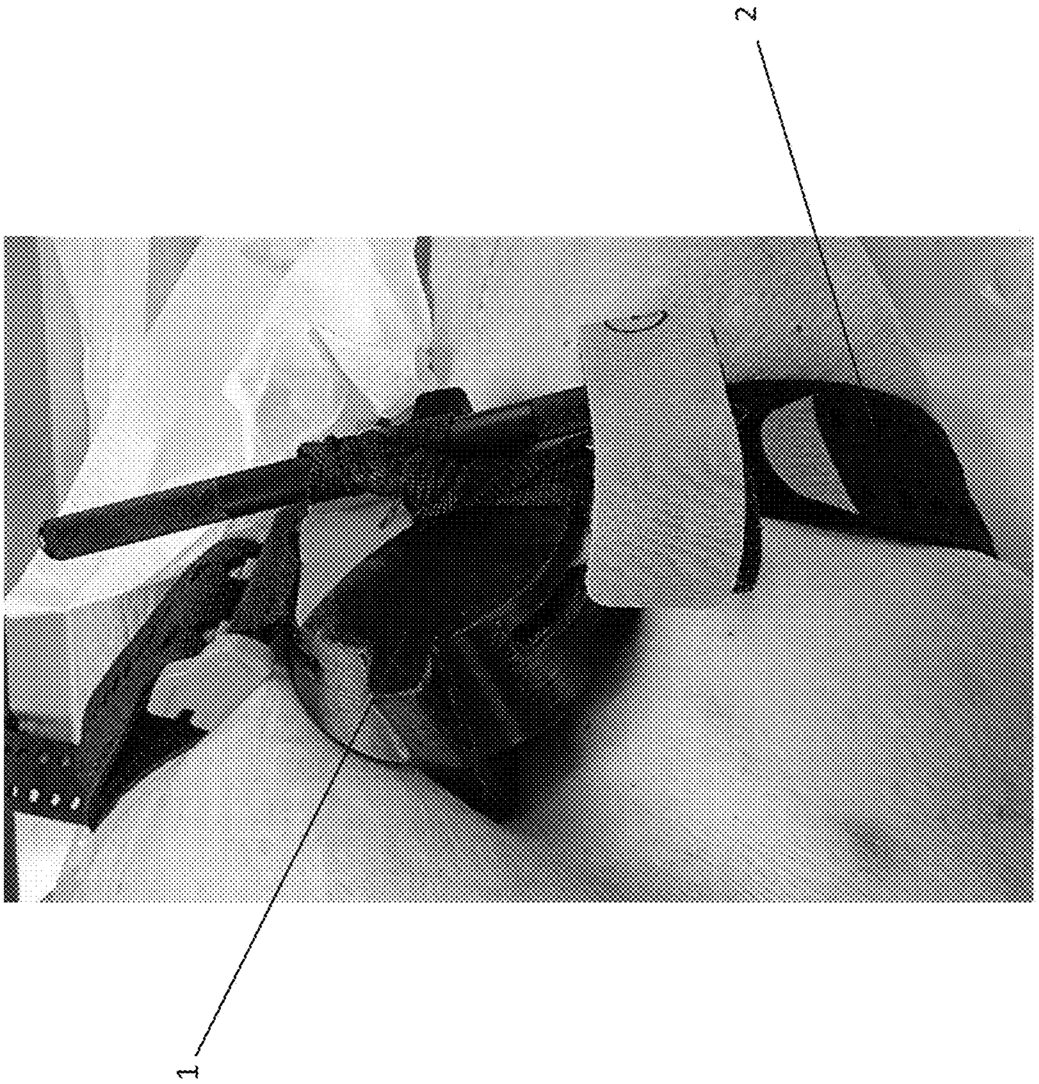
FIG. 11 is a perspective view of the direct pressure device of the present invention in use using an alternate method.

The SAM-XT application is shown in FIG. 11. Attach the two TQs 2 together: insert the tip of the second TQ's band through the first TQ's buckle. Feed the TQ band through the buckle until the tip of the band touches the windless clip but does not pass. Secure the hook and loop material back onto itself to ensure the TQ is close to appropriate size and to help keep the hook and loop material from sticking to the patient or the provider's uniform. Make sure to activate the locking mechanism by pulling in opposite directions until a click is heard and felt. Once the hook and loop material is secure and the locking mechanism is activated, you are ready to attach the direct pressure device 1.

Attaching the device: hold the direct pressure device 1 in your left hand with the wide portion of the clip face up and toward the thumb, with the leaf at the bottom left of the palm. Hold the SAM in the right hand with the buckle facing away from you. Ensure the leaf of the direct pressure device 1 slides under all layers of fabric under the windless and slide the TQ 2 all the way left under the clip. Slide the SAM all the way right if the spring does not fully activate.

Applying the adjunct: now that the direct pressure device 1 is in place, visually inspect to ensure the device is properly prepped. Place the direct pressure device 1 in your right hand with the adjunct facing up and slide it under the patient's lower back, using a sawing motion to work the TQ 2 strap midway down the glute. Ensure the direct pressure device 1 is slightly offset from the desired area/pressure point, to the strap side, not the buckle side, of the device. Place the TQ 2 band through the open buckle, then stabilize the direct pressure device 1 with your non-dominant hand while simultaneously pulling the TQ2 band with your dominant hand. Ensure the TQ 2 is as tight as it can get with no slack before securing the strap back onto itself via the hook and loop material. Once the TQ 2 band is as tight as it can get and the direct pressure device 1 is flat against the patient's skin directly over the desired area/pressure point, secure the hook and loop material all the way around. Twist the windless until the bleeding has stopped. This may take two to six twists, depending on how tight the TQ 2 band was before starting to twist the windless. Finally, secure the windless.

SOF Tourniquet Application

Figure 12:
FIG. 12 is a perspective view of the direct pressure device of the present invention in use using another alternate method.

The SOF tourniquet application is shown in FIG. 12. Attach the two TQs 2 together: insert the tip of the second TQ's band through the first TQ's buckle. Feed the TQ band through the buckle until the tip of the band touches the windless clip but does not pass. Now you are ready to attach the direct pressure device 1.

Attaching the device: hold the direct pressure device 1 in your left hand with the wide portion of the clip face up and toward the thumb, with the leaf at the bottom left of the palm. Hold the SOF in the right hand with the buckle facing away from you. Ensure the leaf of the direct pressure device 1 slides under all layers of fabric under the windless and slide the TQ 2 all the way left under the clip. Push the fabric on the right side of the direct pressure device 1 all the way down under the lip to ensure it is securely in place.

Applying the adjunct: now that the direct pressure device 1 is in place, visually inspect to ensure the device is properly prepped. Place the direct pressure device 1 in your right hand with the adjunct facing up and slide it under the patient's lower back, using a sawing motion to work the TQ 2 strap midway down the glute. Ensure the direct pressure device 1 is slightly offset from the desired area/pressure point, to the strap side, not the buckle side, of the device. Connect the strap to the device as previously discussed, then stabilize the direct pressure device 1 with your non-dominant hand while simultaneously pulling the TQ 2 band with your dominant hand. It will likely take two or three hand positions to ensure the device is properly tightened. Ensure the TQ 2 band is as tight as it can get with no slack. Once the TQ 2 band is as tight as it can get, and the direct pressure device 1 is flat against the patient's skin directly over the desired area/pressure point, twist the windless until the bleeding has stopped. This may take two to six twists, depending on how tight the TQ 2 band was before starting to twist the windless. Finally, secure the windless.

6" ACE Wrap Application

Figure 13:
FIG. 13 is a perspective view of the direct pressure device of the present invention in use using yet another alternate method.
Figure 14:
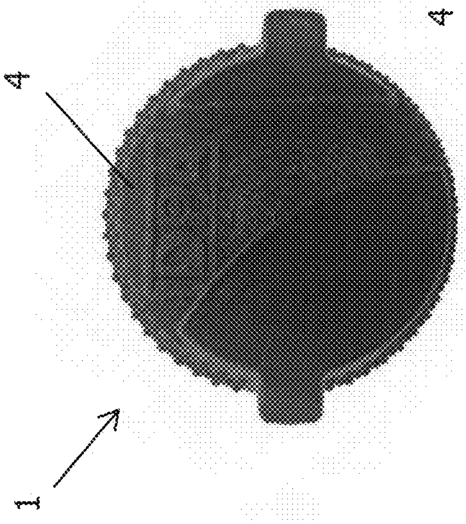
FIG. 14 is a back view of an alternate version of the direct pressure device of the present invention.
Figure 15:
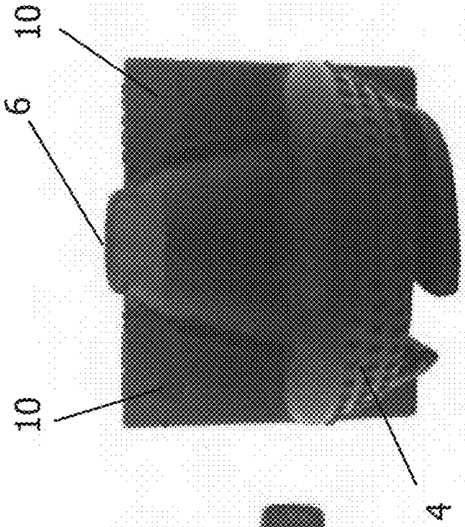
FIG. 15 is a side view thereof.
Figure 16:
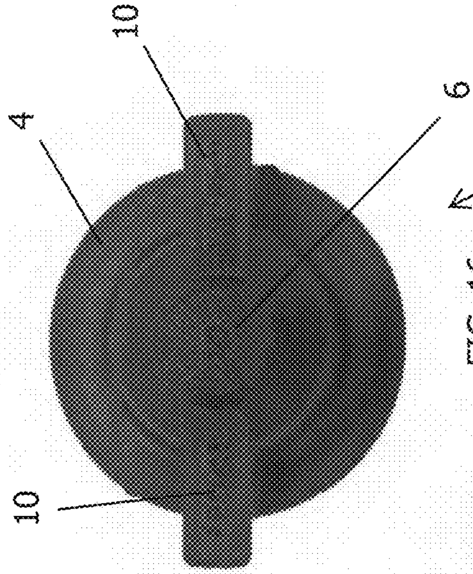
FIG. 16 is a top view thereof.
Figure 17:
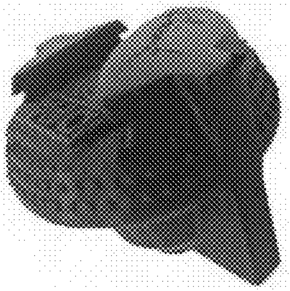
FIG. 17 is a back perspective view thereof.
Figure 18:
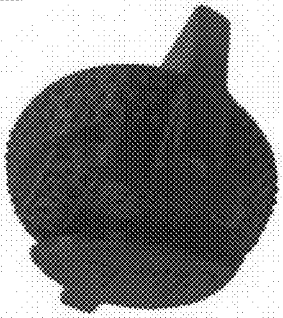
FIG. 18 is an alternate back perspective view thereof.
Figure 19:
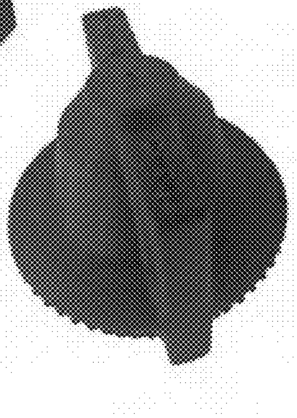
FIG. 19 is a front perspective view thereof.
Figure 20:
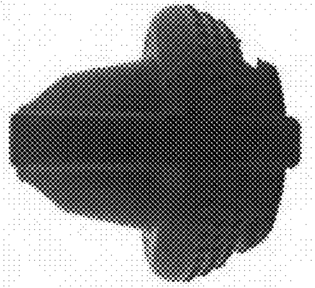
FIG. 20 is an alternate side view thereof.
Figure 21:
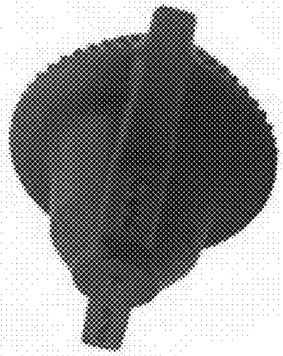
FIG. 21 is an alternate front perspective view thereof.
Figure 22:
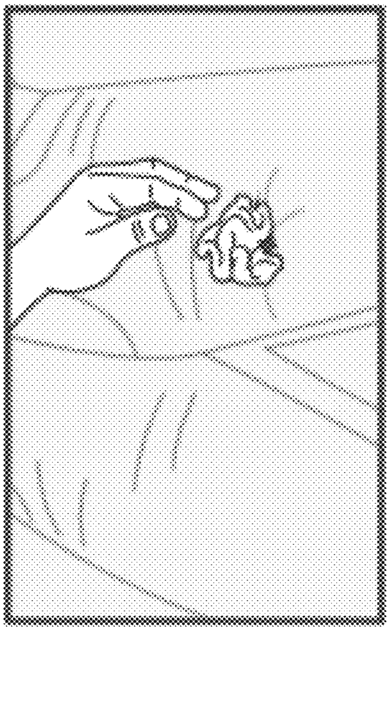
FIG. 22 is a depiction of a first step of a method of using the device.
Figure 23:
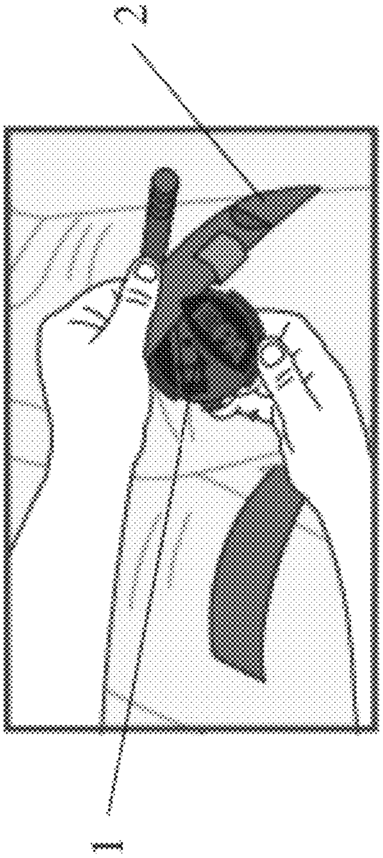
FIG. 23 is a depiction of a second step of a method of using the device.
Figure 24:
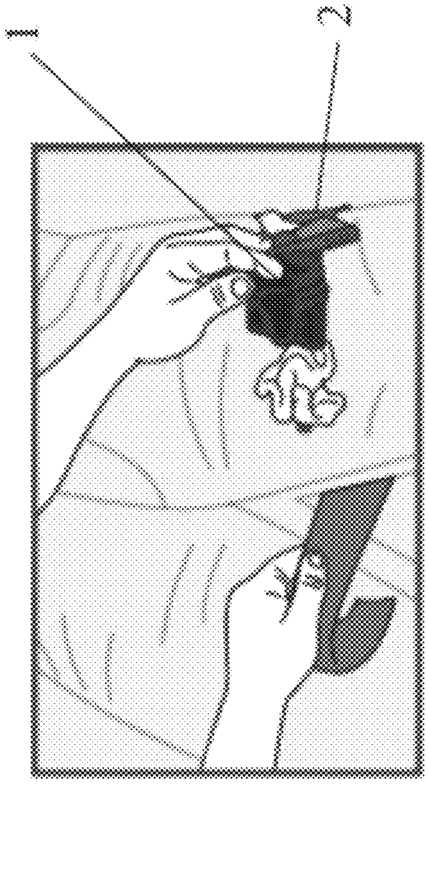
FIG. 24 is a second depiction of a second step of a method of using the device.
Figure 25:
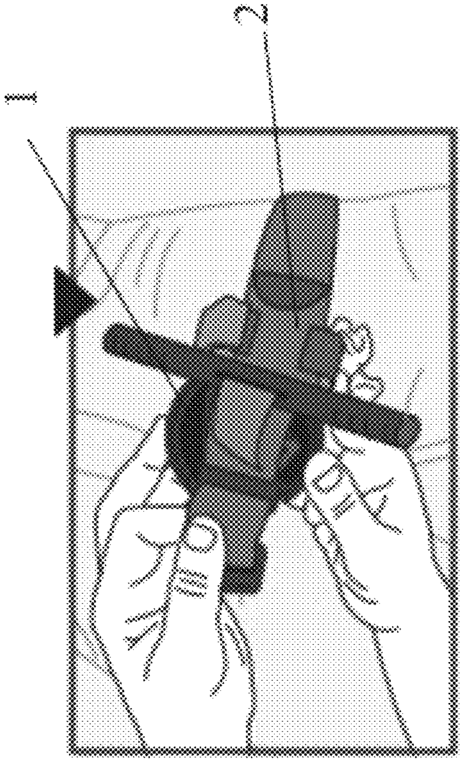
FIG. 25 is a depiction of a third step of a method of using the device.
Figure 26:
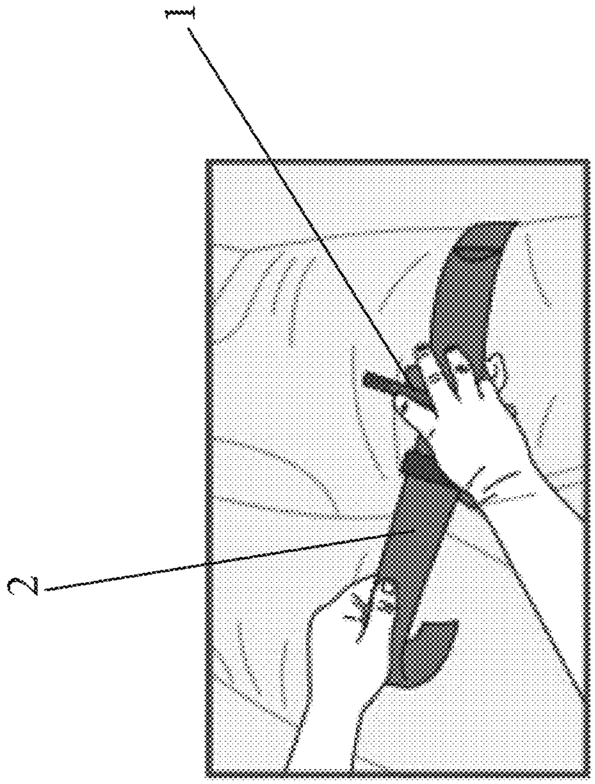
FIG. 26 is a depiction of a fourth step of a method of using the device.

The ACE wrap application is shown in FIG. 13. Ensure the patient's leg is bent, as close to 90 degrees as possible. Place the wrap 3 through the direct pressure device 1 and leave a three to five inch tail. Ensure the tail is placed to the hip. Wrap the ACE wrap 3 around the leg, going to the inside of the leg towards the groin. Once wrapped around the leg back up to the direct pressure device 1, change directions up to the opposite hip and continue around the patient's waist. After going around the waist, use the angle to bring the wrap 3 down over the direct pressure device 1. This will apply a great deal of pressure. Continue to wrap in this pattern until you get close to the end of the wrap 3, then tie the two ends together and straighten the leg. Straightening the legs will increase pressure on the direct pressure device 1 exponentially.

Whereas, the devices and methods have been described in relation to the drawings and claims, it should be understood that other and further modifications, apart from those shown or suggested herein, may be made within the spirit and scope of this invention.

What is claimed is:

1. A direct pressure device comprising:

a deck;

a body projecting perpendicularly from the deck and terminating in an apex, where the body is an apex pylon;

a plurality of apex supports extending at an angle both in a direction of the deck and outward from the apex; and a plurality of cross members extending radially outward from the apex pylon at a location spaced from the deck but closer to the deck than the apex, wherein each of the plurality of apex supports are connected to a respective cross member of the plurality of cross members and extends from the apex to the respective cross member:

where the cross members each terminate in a tie down and where each of the tie downs curve radially outward from the cross member and radially inward towards the deck such that they project outwardly relative to both the apex supports and the deck.

2. The direct pressure device of claim 1 further comprising landing gear extending horizontally outward from the apex or from the apex supports.

3. The direct pressure device of claim 1 where the body is frustoconical.

4. The direct pressure device of claim 3 further comprising a landing gear extending outward from the body.

5. The direct pressure device of claim 1 further comprising a ledge projecting backward and inward from one side of an edge of a back of the deck, where the ledge projects inward to create a gap between a projecting portion of the ledge and the deck.

6. The direct pressure device of claim 1 further comprising a blade connected to one side of an edge of a back of the deck, where the blade projects inward to lie in a plane parallel to, but spaced from, the deck to create a gap therebetween.

7. The direct pressure device of claim 1 further comprising one or more tourniquets and/or elastic wraps.

8. A direct pressure device comprising:

a deck;

a body projecting perpendicularly from the deck and terminating in an apex, where the body is an apex pylon;

a plurality of apex supports extending at an angle both in a direction of the deck and outward from the apex;

a plurality of cross members extending radially outward from the apex pylon at a location spaced from the deck but closer to the deck than the apex, wherein each of the plurality of apex supports are connected to a respective cross member of the plurality of cross members and extends from the apex to the respective cross member; and a landing gear extending horizontally outward from the apex or from the apex supports, where the landing gear is L-shaped, connecting on one end to the apex or one of the apex supports and on an opposing end to one of the cross members.

* * * * *